United States Patent [19]

Negus et al.

[11] Patent Number: 5,219,347
[45] Date of Patent: Jun. 15, 1993

[54] DECOUPLED DUAL-BEAM CONTROL SYSTEM

[75] Inventors: Charles Negus, Framingham; Stephen M. Perez, Taunton, both of Mass.

[73] Assignee: Laser Engineering, Inc., Milford, Mass.

[21] Appl. No.: 813,434

[22] Filed: Dec. 24, 1991

[51] Int. Cl.⁵ .......................................... A61B 17/36
[52] U.S. Cl. ...................................... 606/17; 606/18; 606/19
[58] Field of Search ............................ 606/17, 18, 19; 350/636

[56] References Cited

U.S. PATENT DOCUMENTS

| | | | |
|---|---|---|---|
| 3,710,798 | 1/1973 | Bredemeir | 606/18 |
| 4,289,378 | 9/1981 | Remy | 606/17 |
| 4,526,447 | 7/1985 | Taylor | 606/18 |
| 4,597,380 | 7/1986 | Raif | 606/18 |

Primary Examiner—Peter A. Aschenbrenner
Assistant Examiner—Mike Peffley
Attorney, Agent, or Firm—Iandiorio & Dingman

[57] ABSTRACT

A decoupled dual-beam control system for a compact micromanipulator unit for a surgical laser system includes a focusing mechanism for focusing a first laser beam of a first wavelength at a predetermined focal point; and a control mechanism for directing a second laser beam of a second wavelength onto the focusing mechanism; the control mechanism includes a device for varying the diameter and wavefront of the second laser beam at the focusing mechanism for enabling the focusing mechanism to focus the second beam in the same focal plane as the first beam. The control mechanism further includes a device for translating the second beam relative to the focusing mechanism for enabling the focusing mechanism to coincidentally position the foci of the surgical and aiming beams in the focal plane.

40 Claims, 8 Drawing Sheets

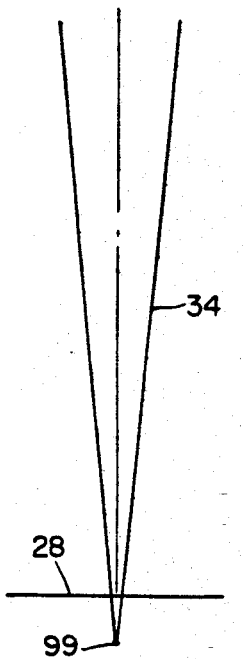
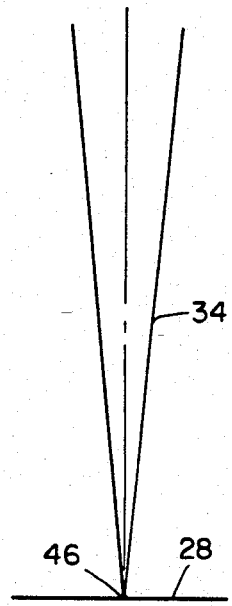
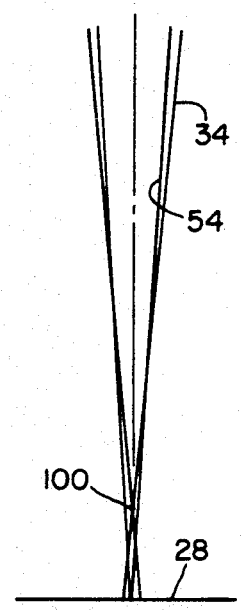
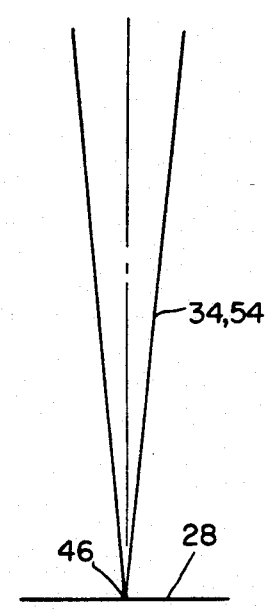
Fig. 6A  Fig. 6B  Fig. 6C  Fig. 6D
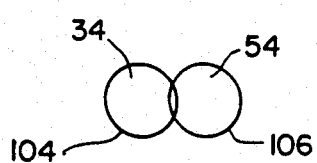
Fig. 6E  Fig. 6F 200 mm f.l.
Primary ZnSe Optic 300mm f.l.
Primary ZnSe Optic 400mm f.l.
Primary ZnSe Optic

DECOUPLED DUAL-BEAM CONTROL SYSTEM

FIELD OF INVENTION

This invention relates to an improved micromanipulator unit for a surgical laser system, and more particularly to such a decoupled dual beam control system which effects coincidence of alignment and focus of two beams, such as a surgical and an aiming beam, without the need of maintaining coincidence throughout the entire laser beam delivery system.

BACKGROUND OF INVENTION

Micromanipulators are used in surgical lasers to precisely focus and position surgical laser beams. There are a number of problems with such devices. There is often a loss of translational alignment of the laser beam due to the long, complicated optical path through the articulated arm of the surgical laser system. Further, deviations in the path through the arm also result in loss of coincidence between the aiming beam and surgical beam. The aiming beam generally is a harmless visible beam used to indicate the impact spot of the surgical beam. Alignment and coincidence problems are thus compounded because the two beams, although propagated through the same optical path, are affected differently because of their different wavelengths. In one type of surgical laser system the surgical beam is a $CO_2$ infrared beam; the aiming beam is a HeNe beam of visible red light. These problems have been exacerbated by the increasing demand for ever-smaller focal diameters of the surgical beam.

One attempt to address these problems uses an achromatic lens system to manipulate the two beams to the same focus by compensating for the inherent variation of the effect of the optical system on the two different wavelengths. For $CO_2$/HeNe lasers, salt lenses are often used. These lenses are expensive and very sensitive to humidity, so they must be operated in an airtight chamber. While this approach compensates for misalignment due to wavelength differences, it does not sufficiently address the problem of overall system alignment. Further, the physician can only adjust for minor mechanical misalignments. For more significant misalignments, equipment servicing is required and the whole system is lost to surgery until readjustment can be effected.

In another approach a virtual image of an aiming beam is used to indicate the impact spot of the surgical beam. Since there is no HeNe beam or any other aiming beam the coincidence problems are obviated. But without the real aiming beam the plane of focus cannot be determined with sufficient certainty: the focal plane can only be determined to an accuracy within the depth of field of the microscope employed in the micromanipulator, which could range up to 10 to 20 mm. Further, the virtual aiming beam does not reflect the true size of the surgical beam, so that during defocusing, to decrease power from cutting level down to cauterizing level for example, there is no accurate indication of spot size. In both approaches the systems are operable only for a specific working distance of the microscope of the micromanipulator system. If another working distance is required the micromanipulator must be changed.

SUMMARY OF INVENTION

It is therefore an object of this invention to provide an improved micromanipulator unit for a surgical laser system.

It is a further object of this invention to provide an improved micromanipulator unit which enables easier, accurate coincidence of alignment and of focus of the surgical and aiming laser beams.

It is a further object of this invention to provide an improved micromanipulator unit which independently aligns and focuses the beams.

It is a further object of this invention to provide an improved micromanipulator unit which enables coincidence of alignment and focus of beams of different wavelength.

It is a further object of this invention to provide an improved micromanipulator unit which enables more accurate aiming and thus functions well with much narrower beams.

It is a further object of this invention to provide an improved micromanipulator unit in which the coincidence of alignment and focus of the aiming and surgical beams projected to the patient are independent of the alignment of the optics in the articulated laser delivery arm.

It is a further object of this invention to provide an improved micromanipulator unit in which the coincidence of alignment and focus of the aiming and surgical beams projected to the patient is effected even with one beam supplied through the laser delivery arm and the other beam generated locally.

It is a further object of this invention to provide an improved micromanipulator unit in which the alignment of the beams can be adjusted without disturbing the optical axis alignment.

It is a further object of this invention to provide an improved micromanipulator unit in which the surgical beam can be defocused without disturbing the focus setting.

It is a further and more general object of this invention to provide a decoupled dual beam control system which independently controls the path and the focus of each beam.

It is a further object of this invention to provide such a decoupled dual beam control system which does not require precisely equal treatment of each beam in order to obtain precise coincidence in alignment and focus.

It is a further object of this invention to provide an improved micromanipulator unit which functions even with beams from separate sources.

The invention results from the realization that a truly accurate and reliable coincident alignment and focusing of two laser beams of different wavelength can be effected, such as for a micromanipulator unit for a surgical laser system, using a decoupled, dual beam control system in which the first beam such as the surgical beam is focused at a focal plane by a focusing mechanism and the second beam such as the aiming beam is manipulated prior to submission to the focusing mechanism to assure that it will focus coincidentally aligned with and on the same focal plane as the first beam.

This invention features a compact micromanipulator unit for a surgical laser system including a focusing mechanism for focusing a surgical laser beam of a first wavelength at a predetermined focal plane; and a control mechanism for directing an aiming laser beam of a second wavelength onto the focusing mechanism. The control mechanism includes means for varying the diameter and wavefront of the aiming laser beam at the focusing mechanism for enabling the focusing mechanism to focus the aiming beam in the same focal plane as the surgical beam. The control mechanism also includes a means for translating the aiming beam relative to the focusing mechanism for enabling the focusing mechanism to coincidentally position the foci of the surgical and aiming beams in the focal plane.

In a preferred embodiment, the focusing mechanism may include a first lens means for receiving both the surgical and aiming beams and a second lens means for receiving and varying the position of the focal plane for the surgical beam. The first lens means may include a positive lens and the second lens means may include a negative lens. The means for varying the diameter and the wavefront of the aiming beam may include third lens means and the means for translating may include reflection means. The reflection means may be transparent to the first wavelength of the surgical beam and it may be located in the path of the surgical beam in the focusing mechanism. The first wavelength may be in the infrared range and the second wavelength may be in the visible spectrum. The focusing mechanism may include an aiming device for directing both beams to the focal plane. The aiming device may include an optical element for redirecting the beams and a gimbal mechanism for moving the optical element in two dimensions about a quiescent point where the beams impinge. The gimbal mechanism may include a first member which pivotably supports the optical element about an axis through the quiescent point and a second member which pivotably supports the optical element about an axis spaced from the quiescent point. The gimbal mechanism may include means for mounting the first member to enable rotation of the quiescent point pivot axis about the quiescent point, and to prevent translation of the quiescent point along the longitudinal axis transverse to the quiescent axis. The gimbal mechanism may also include actuator means linked to the first and second members for rotating the first member about the longitudinal axis and translating along said longitudinal axis said second member transversely to said pivot axis remote from said quiescent pivot axis. The surgical laser beam may originate at a source remote from the focusing mechanism and the laser aiming beam may originate at a source proximate the focusing mechanism in the micromanipulator unit. The micromanipulator unit may further include means for varying the distance between the aiming device and the focusing mechanism for defocusing the surgical laser beam. The micromanipulator unit may further include means for separating the beams and directing the surgical beam to the focusing mechanism and the aiming beam to the control mechanism.

The invention also features a surgical laser system including a surgical laser beam source for supplying a surgical laser beam of a first wavelength, and an aiming laser beam source for supplying an aiming laser beam of a second wavelength. There is a focusing mechanism for focusing the surgical laser beam at a predetermined focal plane. A control mechanism directs the aiming beam onto the focusing mechanism. The control mechanism includes means for varying the diameter and wavefront of the aiming laser beam at the focusing mechanism for enabling the focusing mechanism to focus the aiming beam in the same focal plane as the surgical beam. The control mechanism also includes means for translating the aiming beam relative to the focusing mechanism for enabling the focusing mechanism to coincidentally position the foci of the surgical and aiming beams in the focal plane.

The focusing mechanism may include first lens means for receiving both the surgical and aiming beams and a second lens means for receiving and varying the position of the focal plane for the surgical beam. The first lens means may be a positive lens and the second may be a negative lens. The means for varying the diameter and wavefront of the aiming beam may include third lens means and the means for translating may include reflection means. The reflection means may be transparent to the first wavelength of the surgical beam and may be located in the path of the surgical beam in the focusing mechanism. The first wavelength may be in the infrared range and the second wavelength may be in the visible spectrum. The focusing mechanism may include an aiming device for directing the beams to the focal point. The aiming device may include an optical element for redirecting the beams and a gimbal mechanism for moving the optical element in two dimensions about a quiescent point where the beams impinge. The gimbal mechanism may include a first member which pivotably supports the optical element about an axis through the quiescent point and a second member which pivotably supports the optical element about an axis spaced from the quiescent point. The gimbal mechanism may include means for mounting the first member to enable rotation of the quiescent pivot axis about the quiescent point and to prevent translation of the quiescent point along a longitudinal axis transverse to the quiescent axis. The gimbal mechanism may also include an actuator means linked to the first and second members for rotating the first member about the longitudinal axis and translating along the longitudinal axis a second member transversely to the pivot axis remote from the quiescent pivot axis. The surgical laser beam may originate at a source remote from the focusing mechanism and the aiming laser beam source may be proximate the focusing mechanism. The system may further include an articulated arm for delivering the surgical laser beam to the focusing mechanism. There may be means for varying the distance between the aiming device and the focusing mechanism for defocusing the surgical laser beam. Both the surgical and the aiming laser beams may be delivered through an articulated arm and there may be further included means for separating the beams and directing the surgical beam to the focusing mechanism and the aiming beam to the control mechanism.

The invention more broadly features a decoupled dual beam control system including a focusing mechanism and a control mechanism. The focusing mechanism focuses a first laser beam of a first wavelength at a predetermined focal plane. The control mechanism directs a second laser beam of a second wavelength onto the focusing mechanism. The control mechanism includes means for varying the diameter and wavefront of the second beam at the focusing mechanism to enable the focusing mechanism to focus the second beam in the same focal plane as the first beam. The focusing mechanism further includes means for translating the second beam relative to the focusing mechanism for enabling the focusing mechanism to coincidentally position the foci of the first and second beams in the focal plane.

The focusing mechanism may include first lens means for receiving both the first and second beams and a second lens means for receiving and varying the position of the focal plane for the first beam. The first lens means may be a positive lens and the second lens means may be a negative lens. The means for varying the diameter and wavefront of the second beam may include third lens means and the means for translating may include reflection means. The reflection means may be transparent to the first wavelength of the first beam and may be located in the path of the first beam in the focusing mechanism. The first wavelength may be in the infrared range and the second in the visible spectrum. The first beam may be a surgical beam and the second beam may be an aiming beam for locating the surgical beam. The focusing mechanism may include an aiming device for directing the beams to the focal plane. The aiming device may include an optical element for redirecting the beams and a gimbal mechanism for moving the optical element in two dimensions about a quiescent point where the beams impinge. The gimbal mechanism may include a first member which pivotably supports the optical element about an axis through the quiescent point, and a second member which pivotably supports the optical element about an axis spaced from the quiescent point. There may also be means for mounting the first member to enable rotation of the quiescent point pivot axis about the quiescent point and prevent translation of the quiescent point along the longitudinal axis transverse to the quiescent axis. There may be actuator means linked to the first and second members for rotating the first member about its longitudinal axis and translating the second member transversely to the pivot axis remote from the quiescent pivot axis. The first laser beam may originate at a source remote from the focusing mechanism and the second laser beam may originate at a source proximate the focusing mechanism. There may be means for varying the distance between the aiming device and the focusing mechanism for refocusing the first laser beam. The first and second beams may be delivered from the same source and a control system may further include means for separating the beam and directing the first beam to the focusing mechanism and the second beam to the control mechanism.

DISCLOSURE OF PREFERRED EMBODIMENT

Other objects, features and advantages will occur to those skilled in the art from the following description of a preferred embodiment and the accompanying drawings, in which.

Figure 3:
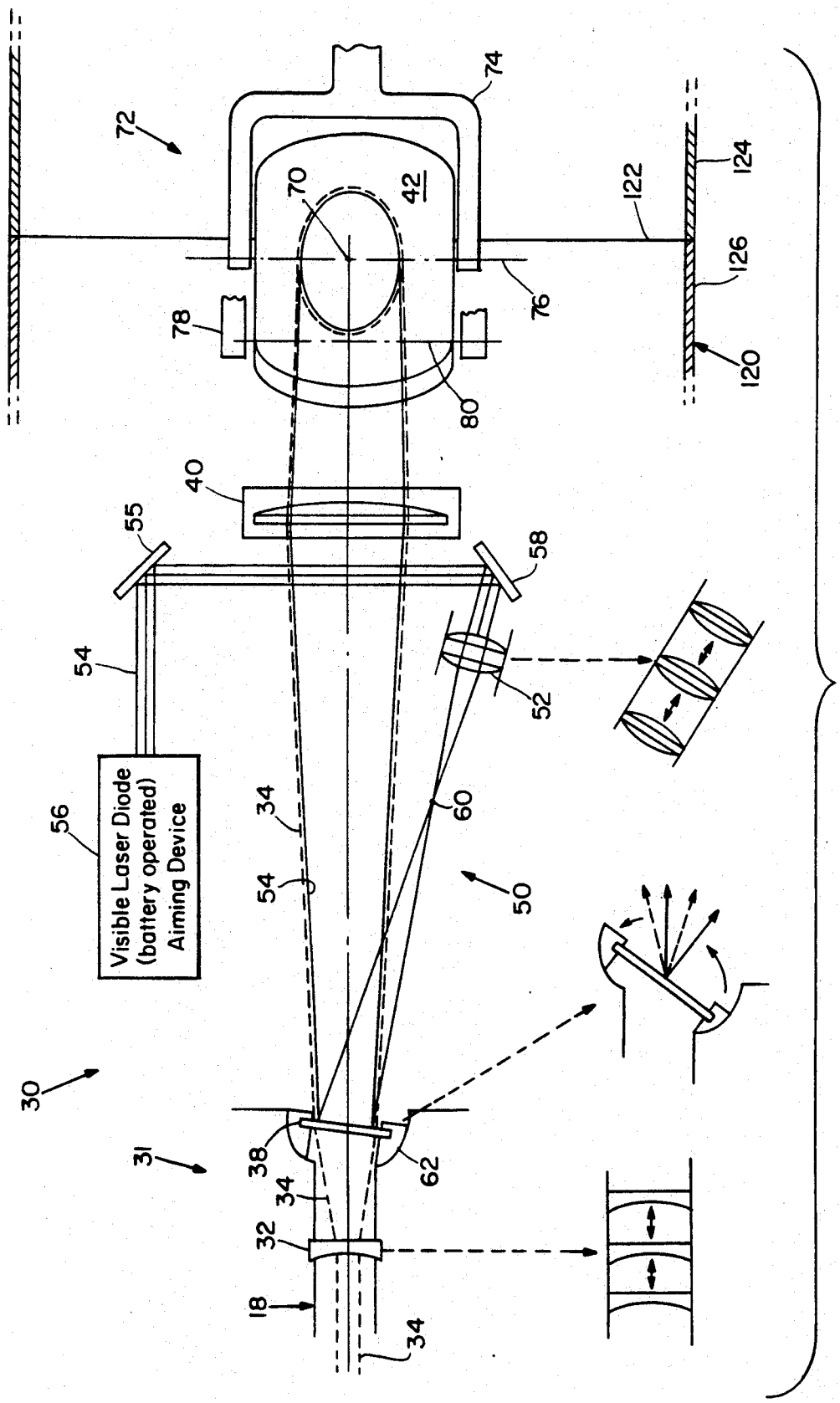
FIG. 3 is a top schematic plan view of the decoupled dual beam control system in the micromanipulator of FIG. 2 with a local aiming beam source.
Figure 7:
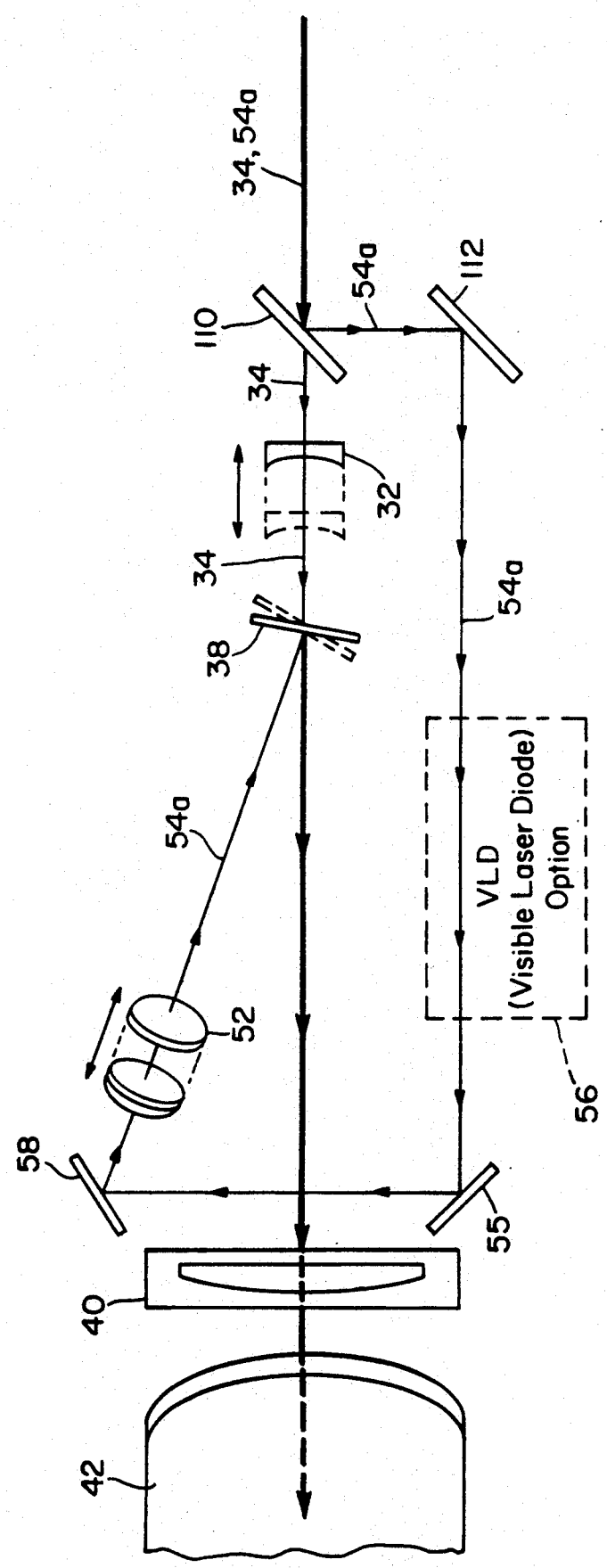
Figure 8:
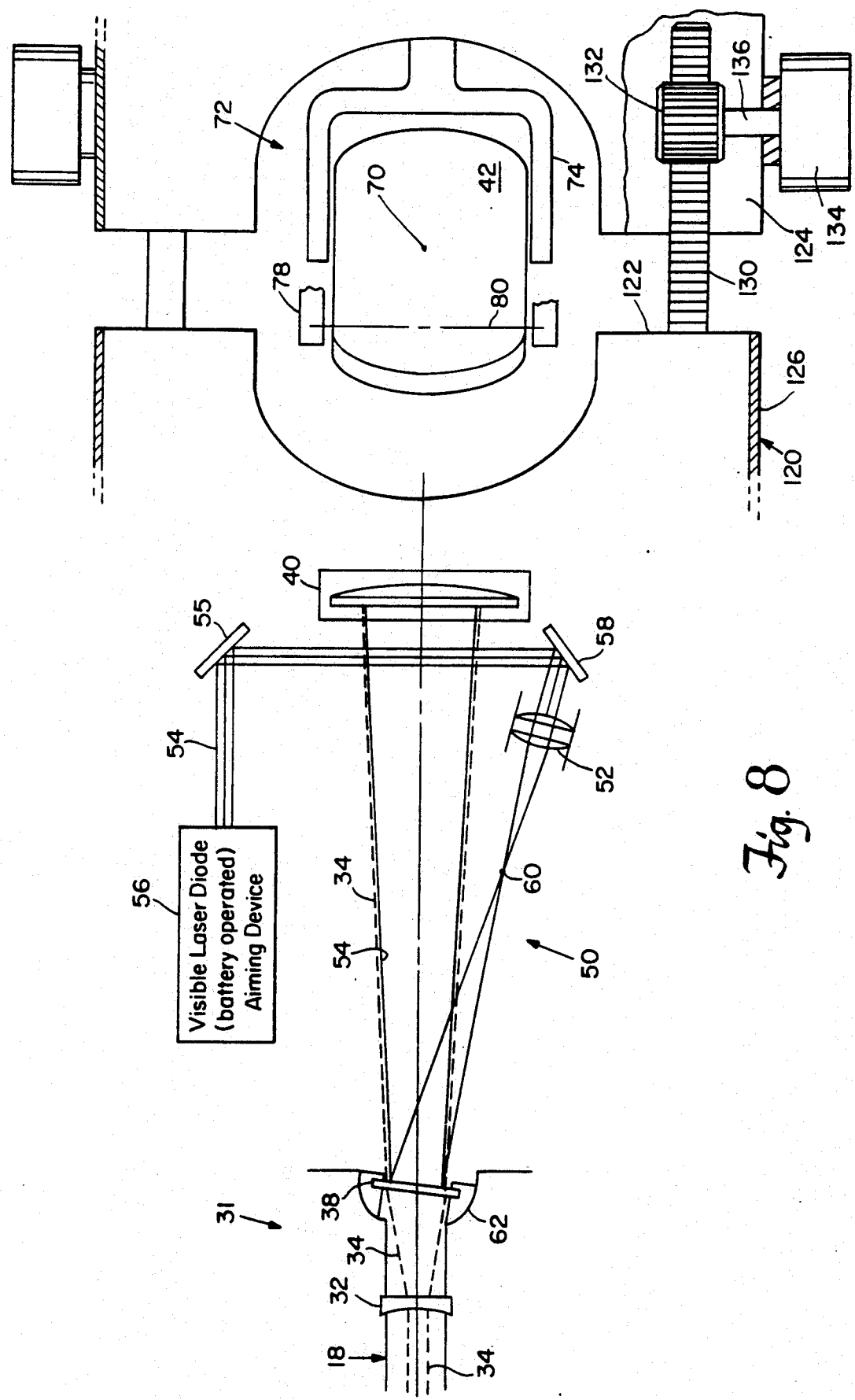
Figure 9A:
Figure 9B:
Figure 9C:

FIGS. 6A–D are side views of the laser beams in various conditions of focus;

FIGS. 6E and F are diagrammatic end views of the laser beams at various conditions of coincidence;

FIG. 7 is a view similar to FIG. 3 with a remote aiming beam source;

FIG. 8 is a view similar to FIG. 3 with the micromanipulator unit partially separated to defocus the beam; and FIGS. 9A–C illustrate in side schematic view three interchangeable focal length modules employing zinc selenide optics.

The invention may be accomplished with a decoupled dual beam control system that has a first mechanism which focuses a primary beam such as a surgical beam at a predetermined focal plane. This focusing mechanism is typically a compound lens with a first lens which expands the beam and projects it onto a second lens which focuses at the desired focal plane and by sizing the beam properly with the first lens so that the beam is at the proper size when it strikes the second lens: the focus at the proper focal plane is obtained. The decoupled dual beam control system also includes a control mechanism which directs the second laser beam such as an aiming beam onto a part of the focusing mechanism, typically the second lens. The control mechanism includes a focusing lens which varies the diameter of the aiming beam that is projected on the second lens of the focusing mechanism. This enables the aiming beam to be focused in precisely the same plane as the surgical beam. In addition, the control mechanism includes means for translating the second beam relative to the second lens in the focusing mechanism for enabling the focusing mechanism to coincidentally position the foci of the first and second beams in the focal plane. This means for translating is typically a mirror (transparent to the primary beam) which can be moved in two dimensions to properly align the projection of the aiming beam with the surgical beam on the second lens so they are both not only focused at the same focal plane, but also in relation with each other at that focal plane so that there will be coincidence both of focal distance and of lateral position.

The primary or surgical beam and the secondary or aiming beam are typically of different wavelengths. For example, the surgical beam may be a $CO_2$ laser beam having a wavelength of 10.6 m and the aiming beam may be a helium neon laser beam having a wavelength of 0.6328 m. Or, the aiming beam may be a visible laser diode beam having a wavelength of 0.670 m. The various optical elements may be simple or compound elements and they may include lenses, combiners, mirrors, or prisms to perform the necessary focusing/defocusing, reflection and redirecting of beams. The final aiming mirror is mounted in a gimbal structure which permits it to be rotated in two dimensions about a quiescent point where the beams impinge so that even if the beam is swept around on the focal plane, the alignment of the beams is not disturbed. This is accomplished by providing one pivotal axis for the mirror which runs right through the quiescent point, and a second pivotal axis which is remote from the first quiescent pivotal axis and generally parallel to it. By rotating the quiescent pivotal axis but not translating it and by rotating and/or translating the second pivotal axis, the stabilization of the quiescent point is achieved while enabling the mirror to perform its function of sweeping the beam over the focal plane of the patient. The same mirror is employed in conjunction with a rack and pinion device to defocus the beam when the surgeon requires less power density or larger spot size at the focal plane of the patient. This can be done by moving the aiming mirror away from the rest of the focusing mechanism slightly to defocus the beam yet preserve the overall focus that has been obtained at some effort using the focusing mechanism and the control mechanism to bring into coincidence the aiming and surgical beams.

Figure 1:
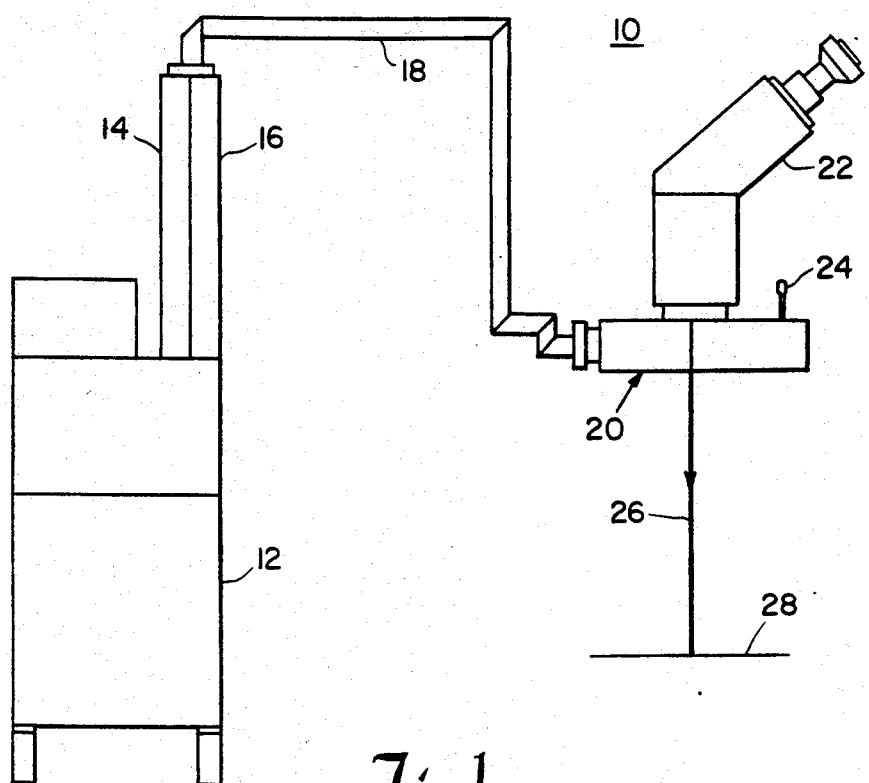
FIG. 1 is a schematic diagram of a surgical laser system with a micromanipulator unit that includes the decoupled dual beam control system according to this invention.
Figure 2:
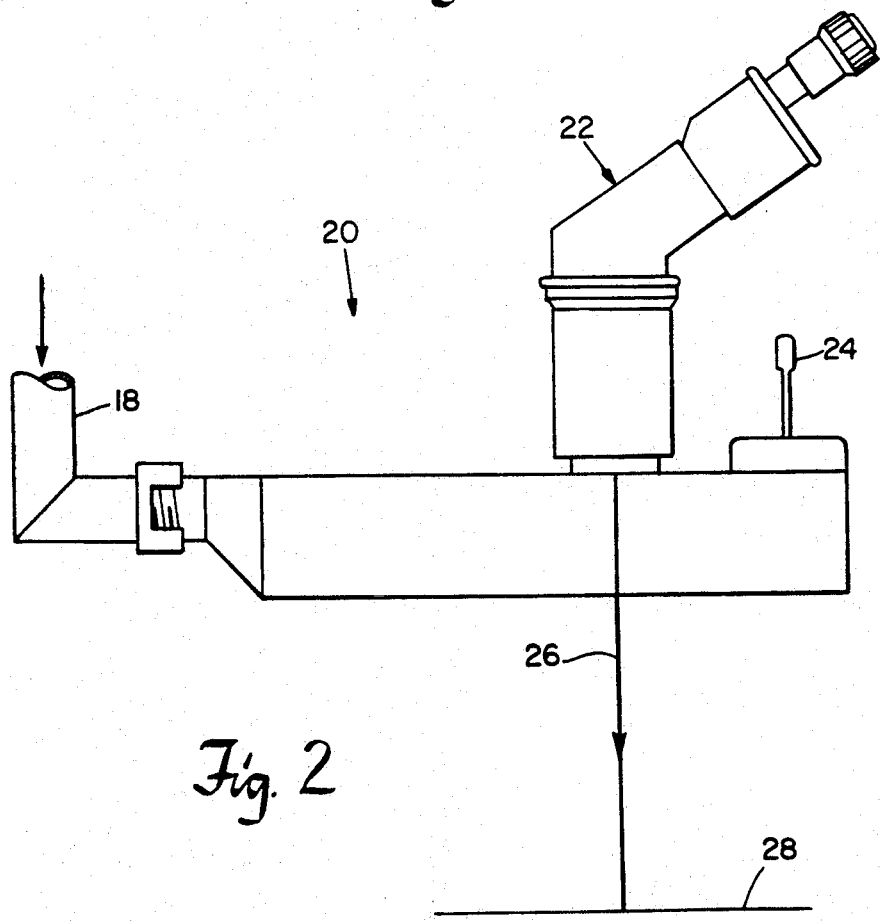
FIG. 2 is an enlarged view of the micromanipulator unit of FIG. 1.

There is shown in FIG. 1 a surgical laser system 10 including a power supply and control housing 12, a $CO_2$ surgical laser 14, and helium neon aiming laser 16, whose beams are delivered through articulated arm 18 to a micromanipulator unit 20 which has associated with it a microscope 22, FIGS. 1 and 2. A gimballed joystick 24 is used to control the beam which is projected along path 26 and focused at focal plane 28 as can be seen in enlarged detail in FIG. 2.

Figure 4:
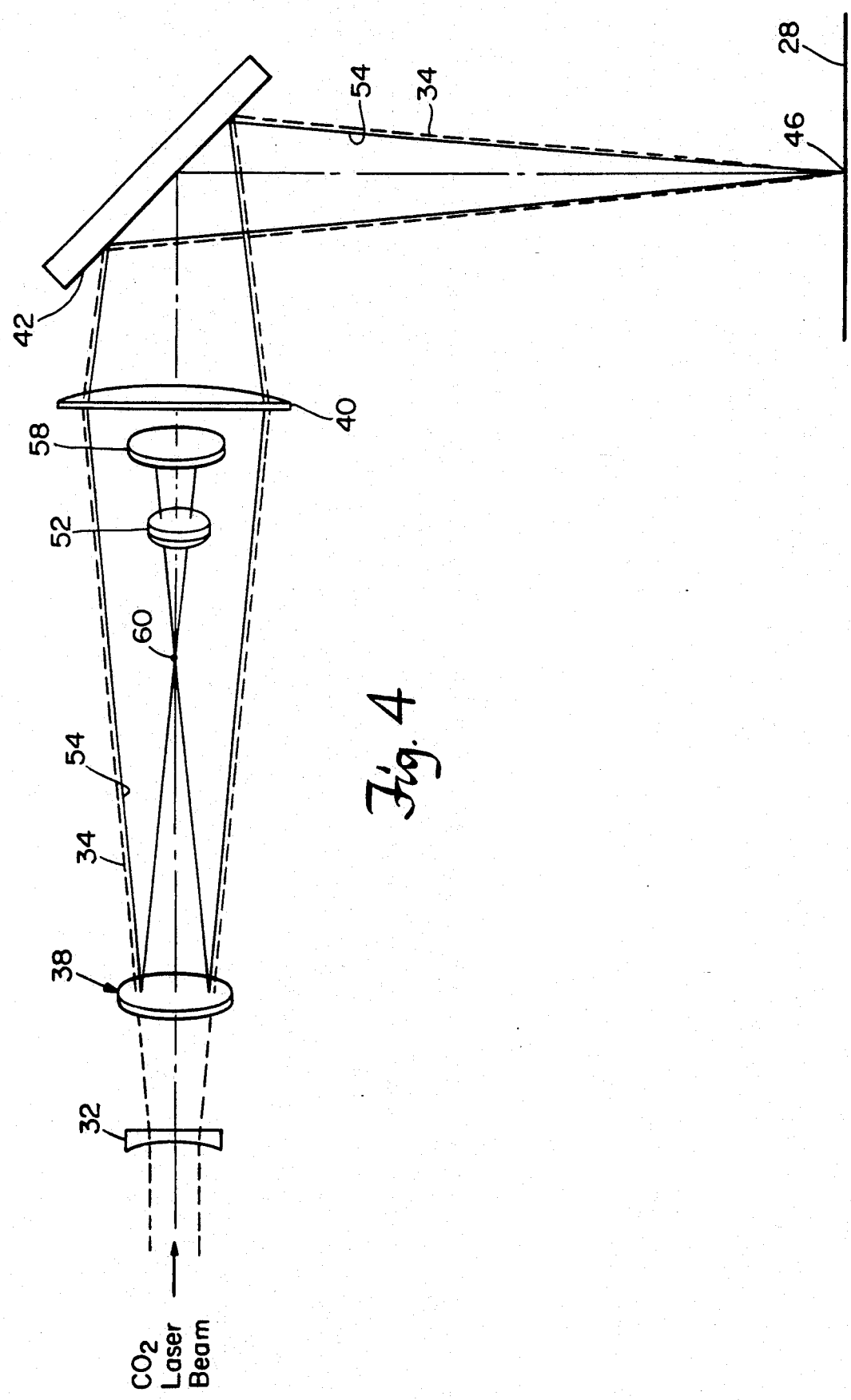
FIG. 4 is a side elevational view of the decoupled dual beam control system of FIG. 3.

In one embodiment, micromanipulator 20 includes a decoupled dual beam control system 30 having a focusing mechanism 31 with negative germanium lens 32 that receives and expands the $CO_2$ surgical beam 34 of wavelength 10.6 μm from laser 14. The expanded beam 34 is transmitted through transparent plano-plano germanium beam combiner 38 and directed onto an interchangeable zinc selenide lens 40 which directs it onto aiming quartz mirror 42 from whence it is. redirected, FIGS. 3 and 4, to focal plane 28. The use of negative lens 32 to expand beam 34 enables a large field of view to be projected onto lens 40, which in turn enables a very sharp focus 46 to be developed at focal plane 28, thus enabling much sharper, finer operation of the surgical laser system.

Micromanipulator 30 also includes a control mechanism 50, which employs a focusing lens 52, that may in fact be a compound lens, which receives the aiming beam 54 of wavelength 0.670 μm from visible laser diode 56 housed in micromanipulator 30 proximate focusing mechanism 31. The aiming beam 54 is redirected from fixed plano mirrors 56 and 58 to the focusing mechanism 52, which varies the focal point 60 of the beam before it strikes the plano-plano germanium beam combiner 38. From beam combiner 38, beam 54 is directed to lens 40 of the focusing mechanism 31. By varying the focal point 60 with focusing lens 52, the wavefront of aiming beam 54 projected on lens 40 is varied in order to make it generally equal to the projection of beam 34 after passing through lens 40. This ensures that both the aiming beam 54 and the surgical beam 34 are focused at the same point 46 on focal plane 28.

Focusing lens 52 may actually be a combination of lenses or a compound lens system, as may be the negative germanium lens 32 and the other lenses and optical components described herein.

The plano-plano germanium beam combiner 38 is mounted in a universal adjustment mechanism 62 which enables it to be moved in two dimensions through X,Y adjustment in order to properly locate aiming beam 54 on lens 40.

Figure 5:
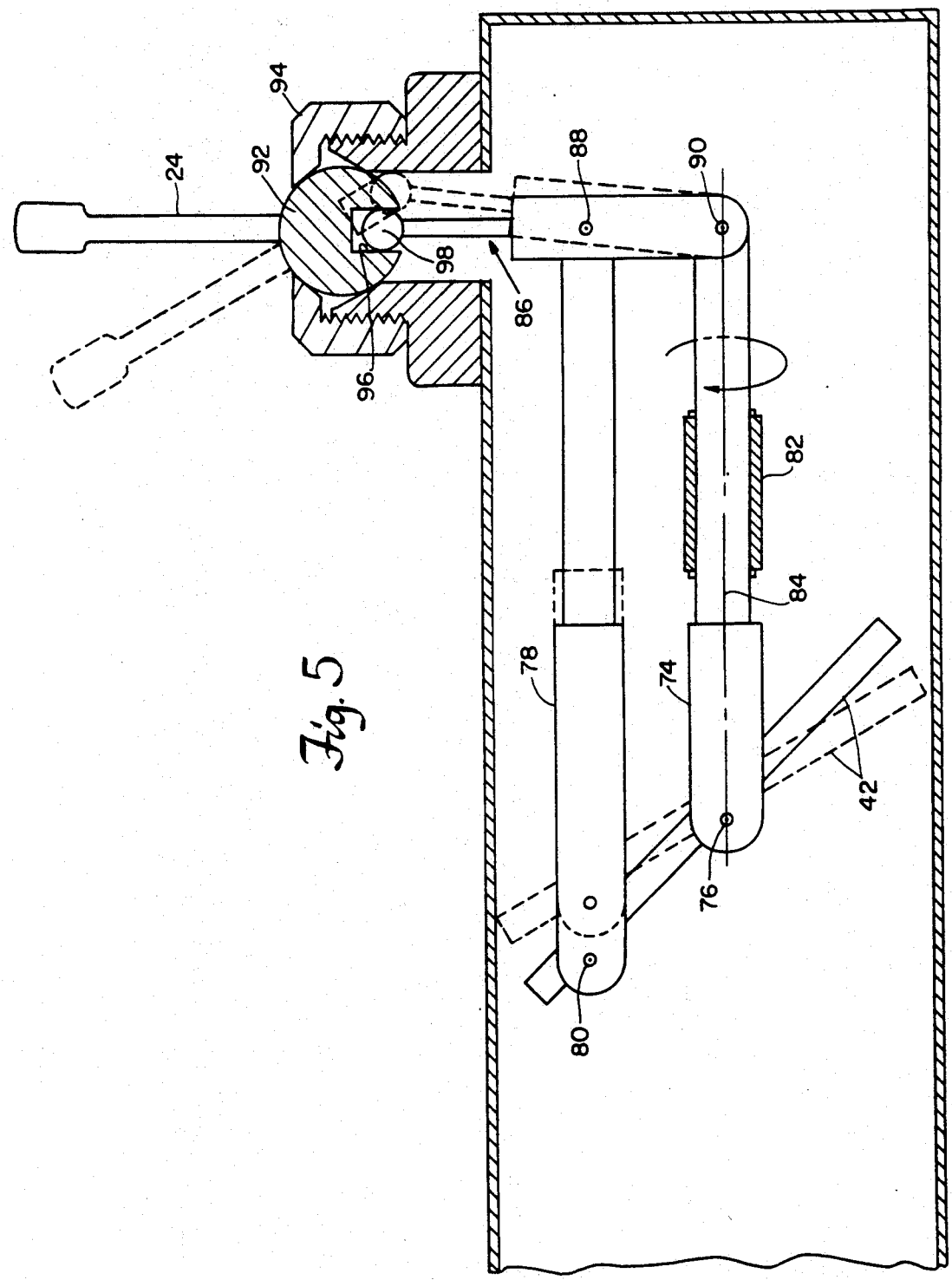
FIG. 5 is a side schematic diagram of the gimbal mechanism shown in FIGS. 3 and 4.

Surgical beam 34 and aiming beam 54 strike aiming mirror 42 centered at point 70, which is a quiescent point about which mirror 42 can be moved in the X and Y dimensions by its gimbal mechanism 72, as shown in FIG. 3 and in more detail in FIG. 5. Mirror 42 is mounted in the first yoke 74, which is pivotably attached to mirror 42 along quiescent pivot axis 76 that passes through quiescent point 70. A second yoke 78 mounts mirror 42 through a second pivot axis 80 which is remote from pivot axis 76. Yoke 74 is installed in mounting 82 which prevents translational movement along longitudinal axis 84 transversely to quiescent axis 76, but enables rotation of yoke 74 about the longitudinal axis 84. In contrast, yoke 78 is free to translate along the direction of longitudinal axis 84. Both yokes 78 and 74 are pivotally attached to actuator 86 at pivots 88 and 90, respectively, The lower part of joystick 24 includes a sphere 92 which is mounted in housing 94 for rotation in two dimensions. This in turn enables recess 96 in sphere 92 to grip smaller sphere 98 at the top of actuator 86 so that actuator 86 may also be moved in two dimensions to provide a two-dimensional capability for positioning mirror 42. In this way, the aiming beam and surgical beam may be, once made coincident with respect to their positions and their foci, easily directable at the focal plane at the patient.

In pre-operation, negative germanium lens 32 is adjusted to bring the focal point of surgical beam 34 to the focal plane 28. Focusing lens 52 is adjusted to focus the aiming beam 54 at the same focal plane 28. Beam combiner 38 is adjusted to position the projection of aiming beam 54 on lens 40 so that the two beams are aligned, that is, they strike the same place on focal plane 28 so that there is coincidence both in focus and in position of the two beams.

For example, in operation if $CO_2$ laser beam 34, FIG. 6A, is focused at point 99 well beyond focal point 28, then lens 32 is adjusted to bring this $CO_2$ surgical laser beam 34 to focus point 46, FIG. 6B, at focal plane 28. If aiming beam 54 is initially improperly focused as at point 100, well above focal plane 28 in FIG. 6C, then lens 52 is adjusted to bring the focus of aiming beam 100 also to focus point 46 at focal plane 28, FIG. 6D.

At this point, surgical beam 34 and aiming beam 54 are coincident as to focal plane, but they may still be not coincident with respect to their lateral position, as shown in FIG. 6E, where the spot 104 of surgical beam 34 and spot 106 of aiming beam 54 at focal plane 28 are shown only slightly overlapping. Complete position coincidence can be obtained by adjusting beam combiner 38 so that the two spots 106 and 104 are in total registration as shown in FIG. 6F.

Although in FIG. 3 the aiming laser source 56 was shown locally present with the focusing mechanism 31 in micromanipulator unit 30, this is not a necessary limitation of the invention. For example, the helium neon laser beam can be propagated down articulated arm 18 along with the beam from surgical laser 14, as shown in FIG. 7, where the helium neon beam 54a is shown more or less coincident with $CO_2$ surgical laser beam 34. A beam splitter mirror 110 passes $CO_2$ surgical laser beam 34 but reflects the helium neon aiming beam 54a which strikes a second mirror 112 that redirects aiming beam 54a to mirrors 55 and 58 as previously. Beam 54a is then directed to the focusing mechanism 52 and thence to beam combiner 38, which redirects it to lens 40. Thus even though the beams both travel down the articulated arm 18, where they may lose coincidence either because of optical irregularities or because of the difference in their wavelengths, this does not affect the coincidence of focus and position at focal plane 28 because the beams are decoupled, that is, they are split at separator 110, and separately focused and projected in order to obtain the same focus and position. A typical HeNe laser operates at a wavelength of 0.6328 m while a $CO_2$ laser operates at a wavelength of 10.6 m.

In order to permit the surgeon to defocus the surgical beam so that, for example, the power applied to patient can be decreased from cutting power to cauterizing power, it is desirable to be able to defocus the surgical beam somewhat. In order to do this without disturbing the delicate focus achieved with the focusing mechanism 31 and control mechanism 50, a means is provided for separating the micromanipulator housing 120 along separation line 122 so that mirror 42 is moved away with portion 124 of the housing from portion 126 of the housing, which houses the focusing lens 40 as well as the rest of the focusing mechanism 30 and control mechanism 50. This is shown in greater detail in FIG. 8, where a rack 130 and pinion 132 are used to draw portion or section 124 with gimbal mechanism 72 and mirror 42 away from section 126 simply by the rotation of the defocusing knob 134, which is connected by shaft 136 to pinion gear 132. After the lower power operation, defocusing knob 134 can be manipulated once again to bring together sections 124 and 126 and reestablish the precise focus that was obtained previously using focusing mechanism 31 and control mechanism 50. Lens 40 in simple or compound form, is a modular device which is easily replaceable by similar modules 40a, 40b and 40c shown in FIGS. 9A, B and C, in order to obtain different focal lengths 200 mm, 300 mm and 400 mm, respectively, for example.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A compact micromanipulator unit for a surgical laser system comprising:
   a focusing mechanism for focusing a surgical laser beam of a first wavelength at a predetermined focal plane;
   a control mechanism for directing an aiming laser beam of a second wavelength onto said focusing mechanism;
   said focusing mechanism including a first lens means for receiving both said surgical and aiming beams and a second lens means for receiving and varying the position of said focal plane for said surgical beam;
   said control mechanism including means for varying the diameter and wavefront of said aiming laser beam at said focusing mechanism for enabling said focusing mechanism to focus said aiming beam in the same said focal plane as said surgical beam; said control mechanism further including means for translating said aiming beam relative to said focusing mechanism for enabling said focusing mechanism to coincidentally position the foci of said surgical and aiming beams in said focal plane.

2. The micromanipulator unit of claim 1 in which said first lens means is a positive lens and said second lens means is a negative lens.

3. The micromanipulator unit of claim 1 in which said means for varying the diameter of said aiming beam includes third lens means and said means for translating includes reflection means.

4. The micromanipulator unit of claim 3 in which said reflection means is transparent to said first wavelength of said surgical beam and is located in the path of said surgical beam in said focusing mechanism.

5. The micromanipulator unit of claim 1 in which said first wavelength is in the infrared range and said second wavelength is in the visible spectrum.

6. The micromanipulator unit of claim 1 in which said focusing mechanism includes an aiming device for directing said beams to said focal plane.

7. The micromanipulator unit of claim 6 in which said aiming device includes an optical element for redirecting said beams and a gimbal mechanism for moving said optical element in two dimensions about a quiescent point where the beams impinge.

8. The micromanipulator unit of claim 7 in which said gimbal mechanism includes a first member which pivotably supports said optical element about an axis through said quiescent point, and a second member which pivotably supports said optical element about an axis spaced from said quiescent point.

9. The micromanipulator unit of claim 8 in which said gimbal mechanism includes means for mounting said first member to enable rotation of said quiescent point pivot axis about the quiescent point and to prevent translation of said quiescent point along a longitudinal axis transverse to said quiescent axis.

10. The micromanipulator unit of claim 9 in which said gimbal mechanism includes actuator means linked to said first and second members for rotating said first member about said longitudinal axis and translating along said longitudinal axis said second member transversely to said pivot axis remote from said quiescent pivot axis.

11. The micromanipulator unit of claim 1 in which said first surgical laser beam originates at a source remote from said focusing mechanism and said second aiming laser beam originates at a source proximate said focusing mechanism in said micromanipulator unit.

12. The micromanipulator unit of claim 6 further including means for varying the distance between said aiming device and said focusing mechanism for defocusing said surgical laser beam.

13. The micromanipulator unit of claim 11 further including means for separating said beams and directing said surgical beam to said focusing mechanism and directing said aiming beam to said control mechanism; said beams being coincidentally aligned prior to separation.

14. A surgical laser system comprising:
   a surgical laser beam source for supplying a surgical laser beam of a first wavelength;
   an aiming laser beam source for supplying an aiming laser beam of a second wavelength;
   a focusing mechanism for focusing said surgical laser beam at a predetermined focal plane; said focusing mechanism including a first lens means for receiving both said surgical and aiming beams and a second lens means for receiving and varying the position of said focal plane of said surgical beam;
   a control mechanism for directing said aiming laser beam into said focusing mechanism; said control mechanism including means for varying the diameter and wavefront of said aiming laser beam at said focusing mechanism for enabling said focusing mechanism to focus said aiming beam in the same said focal plane as said surgical beam; said control mechanism further including means for translating said aiming relative to said focusing mechanism for enabling said focusing mechanism to coincidentally position the foci of said surgical and aiming beams in said focal plane.

15. The surgical laser system of claim 14 in which said first lens means is a positive lens and said second lens means is a negative lens.

16. The surgical laser system of claim 14 in which said means for varying the diameter and wavefront of said aiming beam includes third lens means and said means for translating includes reflection means.

17. The surgical laser system of claim 16 in which said reflection means is transparent to said first wavelength of said surgical beam and is located in the path of said surgical beam in said focusing mechanism.

18. The surgical laser system of claim 14 in which said first wavelength is in the infrared range and said second wavelength is in the visible spectrum.

19. The surgical laser system of claim 14 in which said focusing mechanism includes an aiming device for directing said beams to said focal plane.

20. The surgical laser system of claim 19 in which said aiming device includes an optical element for redirecting said beams and a gimbal mechanism for moving said optical element in two dimensions about a quiescent point where the beams impinge.

21. The surgical laser system of claim 20 in which said gimbal mechanism includes a first member which pivotably supports said optical element about an axis through said quiescent point, and a second member which pivotably supports said optical element about an axis spaced from said quiescent point.

22. The surgical laser system of claim 21 in which said gimbal mechanism includes means for mounting said first member to enable rotation of said quiescent point pivot axis about the quiescent point and to prevent translation of said quiescent point along a longitudinal axis transverse to said quiescent axis.

23. The surgical laser system of claim 22 in which said gimbal mechanism includes actuator means linked to said first and second members for rotating said first member about said longitudinal axis and translating along said longitudinal axis said second member transversely to said pivot axis remote from said quiescent pivot axis.

24. The surgical laser system of claim 14 in which said surgical laser beam originates at a source remote from said focusing mechanism and said aiming laser beam source is proximate said focusing mechanism and said system further includes an articulated arm for delivering said surgical laser beam from said remote source to said focusing mechanism.

25. The surgical laser system of claim 14 further including means for varying the distance between said aiming device and said focusing mechanism for defocusing said surgical laser beam.

26. The surgical laser system of claim 14 further including an articulated arm for transmitting laser beams and in which both said surgical and aiming laser beams are delivered through said articulated arm and said system further includes means for separating said beams and directing said surgical beam to said focusing mechanism and directing said aiming beam to said control mechanism; said articulated arm delivering said laser beams from said sources to said means for separating.

27. A decoupled dual control system comprising:
a focusing mechanism for focusing a first laser beam of a first wavelength at a predetermined focal plane;
a control mechanism for directing a second laser beam of a second wavelength onto said focusing mechanism;
said focusing mechanism including a first lens means for receiving both said first and second beams and a second lens means for receiving and varying the position of said focal plane of said first beam;
said control mechanism including means for varying the diameter and wavefront of said second beam at said focusing mechanism to enable said focusing mechanism to focus said second beam in the same focal plane as said first beam; said control mechanism further including means for translating said second beam relative to said focusing mechanism for enabling said focusing mechanism to coincidentally position the foci of said surgical and aiming beams in said focal plane.

28. The decoupled dual beam control system of claim 27 in which said first lens means is a positive lens and said second lens means is a negative lens.

29. The decoupled dual beam control system of claim 27 in which said means for varying the diameter of said second beam includes third lens means and said means for translating includes reflection means.

30. The decoupled dual beam control system of claim 29 in which said reflection means is transparent to said first wavelength of said first beam and is located in the path of said first beam in said focusing mechanism.

31. The decoupled dual beam control system of claim 27 in which said first wavelength is in the infrared range and said second wavelength is in the visible spectrum.

32. The decoupled dual beam control system of claim 27 in which said first beam is a surgical beam and said second beam is an aiming beam for locating said surgical beam.

33. The decoupled dual beam control system of claim 27 in which said focusing mechanism includes an aiming device for directing said beams to said focal plane.

34. The decoupled dual beam control system of claim 33 in which said aiming device includes an optical element for redirecting said beams and a gimbal mechanism for moving said optical element in two dimensions about a quiescent point where the beams impinge.

35. The decoupled dual beam control system of claim 34 in which said gimbal mechanism includes a first member which pivotably supports said optical element about an axis through said quiescent point, and a second member which pivotably supports said optical element about an axis spaced from said quiescent point.

36. The decoupled dual beam control system of claim 35 further including means for mounting said first member to enable rotation of said quiescent point pivot axis about the quiescent point and to prevent translation of said quiescent point along a longitudinal axis transverse to said quiescent axis.

37. The decoupled dual beam control system of claim 36 further including actuator means linked to said first and second members for rotating said first member about its longitudinal axis and translating said second member transversely to said pivot axis remote from said quiescent pivot axis.

38. The decoupled dual beam control system of claim 27 in which said first laser beam originates at a source remote from said focusing mechanism and said second laser beam originates at a source proximate said focusing mechanism.

39. The decoupled dual beam control system of claim 27 further including means for varying the distance between said aiming device and said focusing mechanism for defocusing said first laser beam.

40. The decoupled dual beam control system of claim 27 in which said first and second beams are delivered from the same source and said control system further includes means for separating said beams and directing said first beam to said focusing mechanism and directing said second beam to said control mechanism.

* * * * *